(12) United States Patent
Seize

(10) Patent No.: US 8,600,611 B2
(45) Date of Patent: Dec. 3, 2013

(54) SYSTEM AND METHOD FOR MEASURING FATIGUE FOR MECHANICAL COMPONENTS OF AN AIRCRAFT AND AIRCRAFT MAINTENANCE METHOD

(75) Inventor: Guilhem Seize, Corbeil-Essonnes (FR)

(73) Assignee: SNECMA, Paris (FR)

( * ) Notice: Subject to any disclaimer, the term of this patent is extended or adjusted under 35 U.S.C. 154(b) by 0 days.

(21) Appl. No.: 13/509,874

(22) PCT Filed: Nov. 15, 2010

(86) PCT No.: PCT/EP2010/067455
§ 371 (c)(1),
(2), (4) Date: May 15, 2012

(87) PCT Pub. No.: WO2011/061141
PCT Pub. Date: May 26, 2011

(65) Prior Publication Data
US 2012/0226409 A1    Sep. 6, 2012

(30) Foreign Application Priority Data

Nov. 17, 2009  (FR) .................................. 09 58123

(51) Int. Cl.
*G01B 7/16* (2006.01)
(52) U.S. Cl.
USPC ....... 701/33.2; 701/33.5; 701/31.1; 701/31.6; 701/8
(58) Field of Classification Search
None
See application file for complete search history.

(56) References Cited

U.S. PATENT DOCUMENTS

| | | | |
|---|---|---|---|
| 3,733,424 A * | 5/1973 | Pitts et al. ........................ | 73/764 |
| 4,336,595 A | 6/1982 | Adams et al. | |
| 4,894,787 A | 1/1990 | Flannelly et al. | |
| 5,111,402 A * | 5/1992 | Brooks et al. ................ | 701/29.2 |
| 5,195,046 A | 3/1993 | Gerardi et al. | |
| 5,531,122 A | 7/1996 | Chatham et al. | |
| 6,449,565 B1 | 9/2002 | Budrow et al. | |
| 6,480,792 B1 | 11/2002 | Prendergast | |
| 6,617,963 B1 * | 9/2003 | Watters et al. ............. | 340/10.41 |
| 6,778,888 B2 * | 8/2004 | Cataldo et al. ............... | 701/29.6 |
| 6,806,808 B1 | 10/2004 | Watters et al. | |

(Continued)

FOREIGN PATENT DOCUMENTS

| | | |
|---|---|---|
| EP | 0 339 833 | 2/1989 |
| EP | 1 791 047 | 5/2007 |
| WO | 00 25272 | 5/2000 |
| WO | 2004 068095 | 8/2004 |

OTHER PUBLICATIONS

International Search Report Issued Mar. 18, 2011 in PCT/EP10/067455 Filed Nov. 15, 2010.

*Primary Examiner* — Helal A Algahaim
*Assistant Examiner* — Rebecca Wagner
(74) *Attorney, Agent, or Firm* — Oblon, Spivak, McClelland, Maier & Neustadt, L.L.P.

(57) ABSTRACT

A system for measuring fatigue of a component of an aircraft subject to mechanical stresses includes: a plurality of stress sensors mounted on the component, each sensor being configured to detect a predetermined mechanical stress threshold and to deliver a data signal representative of exceeding of the threshold; and a mechanism for recording the data and the sensors configured to detect different stress thresholds so as to make it possible to calculate, on the basis of the data recorded by the system, an estimation of fatigue of the component due to the mechanical stresses. It is thus possible to optimize overhaul of the components.

12 Claims, 2 Drawing Sheets

(56) References Cited

U.S. PATENT DOCUMENTS

| | | | |
|---|---|---|---|
| 7,558,701 B2 * | 7/2009 | Andarawis et al. | 702/183 |
| 7,778,751 B2 * | 8/2010 | Murphy et al. | 701/31.4 |
| 7,805,228 B2 * | 9/2010 | Liebl et al. | 701/31.5 |
| 2002/0154029 A1 | 10/2002 | Watters et al. | |
| 2006/0069521 A1 | 3/2006 | Meyer et al. | |
| 2006/0243055 A1 | 11/2006 | Sundermeyer et al. | |
| 2007/0107530 A1 | 5/2007 | Anderson | |
| 2007/0118301 A1 | 5/2007 | Andarawis et al. | |
| 2008/0167833 A1 | 7/2008 | Matsen et al. | |
| 2010/0299086 A1 * | 11/2010 | Oudovikine | 702/42 |
| 2012/0035804 A1 * | 2/2012 | Roberts | 701/33.2 |
| 2012/0101682 A1 * | 4/2012 | Flister et al. | 701/33.2 |

* cited by examiner

SYSTEM AND METHOD FOR MEASURING FATIGUE FOR MECHANICAL COMPONENTS OF AN AIRCRAFT AND AIRCRAFT MAINTENANCE METHOD

BACKGROUND OF THE INVENTION

1. Field of the Invention

The invention relates to a system and a method for measuring fatigue for mechanical components of an aircraft, for example an airplane, and a method for maintaining the aircraft.

Safety rules require airlines to monitor the fatigue of the components of the aircraft that they operate, these components being subjected to a large number of mechanical stresses (or loads). The components are therefore the subject of an overhaul (or maintenance) in a regular and recurrent manner.

2. Description of the Related Art

For example, the components for suspending the turbojets from the airplanes are subjected to strict inspections. Each overhaul of a suspension makes it necessary to stop the operation of the airplane and to remove the suspension in order to carry out the tests. The frequency of the overhauls is determined in advance and an overhaul is carried out systematically on expiration of each preset time period (for example every 2600 flight cycles (takeoff-flight-landing)), irrespective of the real state of fatigue of the component. So as not to take the risk of carrying out an overhaul too long after the appearance of a state of fatigue requiring an intervention such as a repair or a replacement, this time period must be chosen (by computation or empirically) as being the minimum period beyond which there is a risk that the component will break, even if this risk remains statistically marginal. This minimum period therefore corresponds to the situations of the components subjected to accidental stresses; accordingly, many overhauls are carried out on components that could have been used without danger for longer since they have not been subjected to accidental stresses. Finally, in the absence of analysis of the real stresses to which a component has been subjected, the worst case scenario is always taken with respect to the possible damaging of the latter, which leads to overhauls that are often premature.

Moreover, and for safety reasons, the components are used for a shorter period than they could actually be, so that they do not achieve periods of use during which the risk of breakage exceeds a certain threshold. Again, in the absence of analysis of real conditions of use of the components, criteria are chosen that correspond to the worst case scenarios and it is for this reason that conventionally in the aeronautics field a component is replaced halfway through its theoretical service life, irrespective of its real state of fatigue. The final effective profitability of the components (the ratio of the effective usage period of the component over its theoretical capacity) is therefore of the order of 50%, which it would be desirable to improve.

Moreover, because of the frequent overhauls (making it necessary to remove the suspension from an airplane and then to reinstall it on an airplane that is a priori different) and different service lives of the various components of an airplane, the monitoring of the service life of a suspension is complex. In particular, it may happen that the serial number etched on a metal suspension wears off over time; in this case, not being able to refer to its history and in order to take no risk, the estimate of its period of use must be made with the most pessimistic assumptions, for example considering that this suspension was installed in the first airplane fitted with this type of suspension and has flown continuously since then; in practice, the use of the component has been less than this pessimistic notional assumption such that the suspension will be replaced too soon.

Moreover, although there currently exist indirect indicators of the fatigue of suspensions, they can only be approximate and provide uncertain information. Thus, in order to estimate the state of fatigue of a suspension, data are sometimes used that are measured by the inertial unit of the airplane which determines whether the airplane has been subjected to exceptional stresses such as a hard landing; accordingly, a computation of load transfers from the inertial unit to the component is carried out. Nevertheless, although a hard landing may indeed impose exceptional loads on a suspension, it is not systematically the case and one may be induced to overhaul a suspension when the landing has not actually stressed the suspension, for example because the forces have been absorbed and have not been transmitted to the suspension.

The prior art has not truly dealt with the question of measuring the fatigue in order to anticipate the overhauls; it has rather concentrated on detecting the breakage of components, such as for example in patent application FR 2,923,540 in the name of the Applicant.

BRIEF SUMMARY OF THE INVENTION

The object of the invention is to alleviate these drawbacks and to make it easier to measure the fatigue of mechanical components of aircraft in order to improve the pertinence of their overhauls and optimize their use.

The invention applies particularly well to the suspensions of turbojets from airplanes, the components forming these suspensions being subjected to a considerable number of stresses. Nevertheless, the Applicant does not intend to restrict the scope of its rights to just this application, the invention being applied and obtaining advantages in a more general manner to any component of an aircraft subjected to stresses.

Therefore the invention relates to a system for measuring fatigue of an aircraft component subjected to mechanical stresses, the system comprising a plurality of stress sensors mounted on the component, each sensor being arranged to detect a predetermined mechanical stress threshold and to deliver a data signal representative of the violation of this threshold, the system comprising means for recording these data, the sensors being arranged to detect different stress thresholds in order to make it possible to compute, based on the data recorded by the system, an estimate of the fatigue of the component due to the mechanical stresses.

The data recorded by the system are preferably the number of occurrences of violation of each of the thresholds.

It is therefore possible to have a good estimate of the real fatigue of the component associated with the stresses to which it has been subjected. In some way, the sensors can "count" the number of occurrences of stresses violating various thresholds, these occurrences being recorded by the system which makes it possible to deduce therefrom the resultant damage (that is to say the fatigue) to the component. All of the stresses are broken down incrementally, each threshold of a sensor forming one increment.

It is therefore possible to optimize the use of the component. In particular, based on the knowledge of its fatigue, it is possible to decide the appropriateness of the overhaul of a component, this choice being made on the basis of the fatigue actually sustained by the component and not in response to general statistics applied to all the components irrespective of the stresses actually absorbed (whether they be stresses of normal use or accidental or exceptional stresses).

The data recorded by the system also make it possible to replace a component only if its real damage justifies it, unlike the prior art in which the components were scrapped after a predetermined period of time and irrespective of their real state of fatigue.

It is moreover possible to instrument the test aircraft with the system of the invention in order to improve the sizing of the components based on the data recorded by the system. It is also possible, by virtue of the invention, to confirm the values supplied by the aircraft manufacturers for the certification of the components; in particular, if a complex fatigue spectrum is determined by virtue of the method of the invention, this spectrum can be compared to the spectra supplied by the aircraft manufacturers.

It should be noted that, if the serial number of a component is worn off, it is possible to estimate its effective duration of use by an estimate of its fatigue. Moreover, and in particular, the number of nonexceptional stresses to which the component has been subjected gives a good approximation of its period of use.

The increments from one stress threshold to another (that is to say the intervals separating the successive thresholds) may be constant or open-ended. This can make it possible to concentrate the number of sensors on ranges of particular stresses.

According to one particular embodiment, the system comprises a processing unit comprising the data-recording means and the sensors comprise means for transmitting the data to the processing unit.

The processing unit may comprise means for analyzing the data making it possible to compute on the basis of the data an estimate of the fatigue of the component due to the mechanical stresses.

According to another embodiment, each sensor comprises data-recording means.

Preferably, the system (in particular the processing unit or the sensors depending on the chosen embodiment) comprises means for transmitting the data—preferably on request—to remote means for analyzing these data, arranged to compute an estimate of the fatigue of the component. These remote means may for example comprise a portable device held by an operator; it is therefore sufficient for the latter to receive the data from the system on his device in order to ascertain the state of fatigue of the component.

According to a preferred embodiment, the sensors are mechanical deformation sensors.

According to a preferred embodiment, the sensors are of the MEMS type.

The acronym MEMS means "microelectromechanical system". By convention, those skilled in the art refer to these microsystems by the acronym MEMS which will therefore be used in the rest of the description. They are systems incorporating, on a chip, on a miniature scale (of the order of a millimeter or a micrometer), not only electronic computing members, but also mechanical members supplying data to the computing members or controlled by them. These mechanical and electronic members are used to fulfill certain functions, in this instance at least one function of capturing data of mechanical stresses and a function of recording data and/or of transmitting data. The systems of the MEMS type therefore comprise microelectronic and micromechanical members. They are usually manufactured using integrated circuits for the electronic members and using micromachining for the mechanical members.

Since the systems of MEMS type are miniaturized, their space requirement is low, which is advantageous for a component of an aircraft. Another consequence of this low space requirement is that it is easily possible to provide a plurality of sensors on one and the same component and thus improve the accuracy of the measurement, a state of fatigue being broken down into a larger number of stress thresholds.

According to one particular embodiment, at least two sensors are arranged to detect one and the same stress threshold. Thus, in the event of failure of one sensor, the other sensor can still detect the stress threshold in question.

The invention applies particularly well to metal components, the fatigue of which is particularly sensitive to the mechanical stresses that are applied to them.

The invention also relates to a method for measuring fatigue of an aircraft component subjected to mechanical stresses in which:
 the violation of stress thresholds is measured at determined points of the component, the thresholds being different from one point to another,
 the number of occurrences of measurements of violation of each of the thresholds is recorded and
 based on this number of occurrences, an estimate of the fatigue of the component is computed.

Such a maintenance method provides all the advantages of the system described above.

According to a preferred embodiment:
 for each threshold, based on the total number of occurrences, the number of occurrences of measurements of violation of said threshold and that are below the higher threshold are computed and
 for each threshold, the equivalent fatigue of the component corresponding to the application of a number of stresses between these thresholds corresponding to said number of computed occurrences is computed and
 the equivalent fatigues computed are added together to obtain the total fatigue of the component.

According to a preferred embodiment, the method is applied with the aid of the system explained above.

The invention also relates to an aircraft maintenance method comprising at least one component subjected to mechanical stresses and a system for measuring fatigue conforming to the system explained above, in which:
 a request to transmit the data recorded by the system is transmitted to the system,
 the data are received, and
 based on these data, an estimate of the fatigue of the component due to the mechanical stresses is computed.

Such a maintenance method provides all the advantages of the system described above. In particular, it makes it possible to make a decision relating to the appropriateness of an overhaul without removing the component, since it is sufficient to receive the data recorded by the system to ascertain the fatigue of the component.

According to a preferred embodiment, the request is transmitted and the data are received wirelessly by means of a portable transmission/reception device.

The use of such a portable device is particularly simple and allows a user to stand beside the aircraft and simply send requests and receive data in order to control notably the overhauls of the component.

In particular, it is possible to provide that one and the same portable device can be used for the reception of data originating from several systems for measuring fatigue mounted on distinct components. It is therefore possible to control the overhauls of these components in their entirety.

According to a preferred embodiment in this case, the portable device comprises processing means making it possible to compute an estimate of the fatigue of the component.

BRIEF DESCRIPTION OF THE SEVERAL VIEWS OF THE DRAWINGS

The invention will be better understood with the aid of the following description of the preferred embodiment of the system and of the method of the invention, with reference to the appended drawings in which.

DETAILED DESCRIPTION OF THE INVENTION

Figure 1:
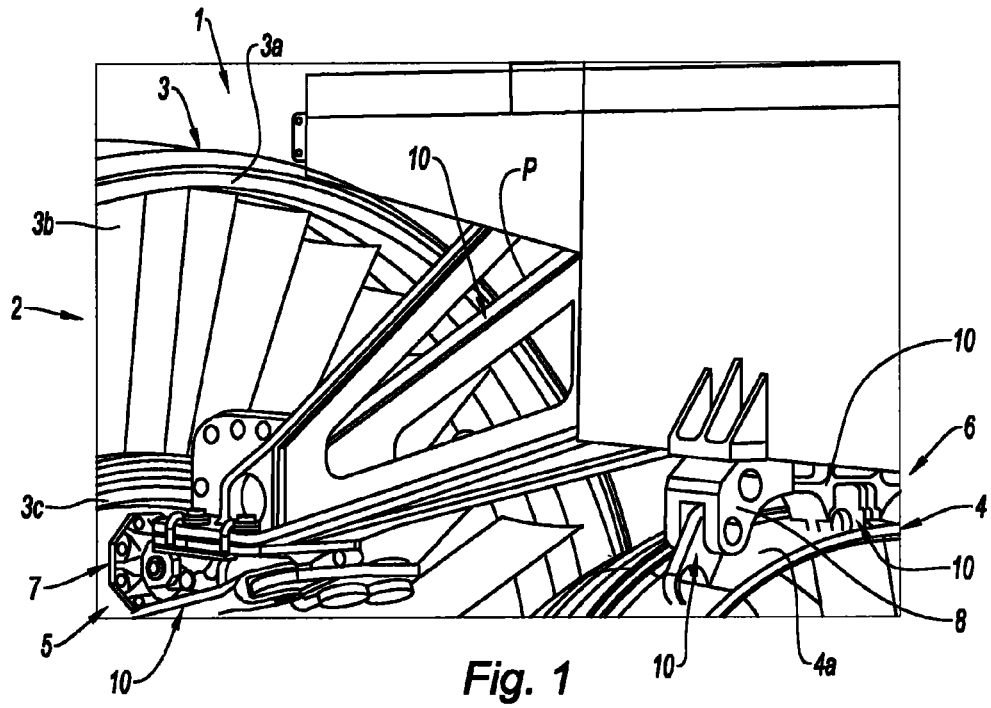
FIG. 1 represents a schematic view in perspective, seen from downstream, of a turbojet suspended from the structure of an aircraft by a first type of suspension.

With reference to FIG. 1, and in a manner well known to those skilled in the art, a turbojet 1 comprises a fan 2 by which the outside air is aspirated into the turbojet, a low-pressure compressor upstream of a high-pressure compressor, these compressors being arranged to compress the air and at the exit of which the compressed air is guided to a combustion chamber where it is burnt with fuel that is also compressed; the burnt gases are guided to a high-pressure turbine then a low-pressure turbine at the exit of which they are expelled from the turbojet through an exhaust nozzle.

The various portions of the turbojet are contained in casings. The turbojet 1 shown in FIG. 1 comprises in particular, upstream, a fan casing and a casing 3 called the intermediate casing and, downstream, an exhaust casing 4. The intermediate casing 3 and the exhaust casing 4 are structural casings of the structure of the turbojet 1.

The intermediate casing 3 comprises an external shroud $3a$ connected by radial arms $3b$ to a hub $3c$ supporting, by means of upstream rolling bearings, the rotor shafts of the low-pressure and high-pressure spools of the turbojet 1. Similarly, the exhaust casing 4 comprises an external shroud $4a$ supporting a hub on which the downstream rolling bearings of the rotor shafts of the low-pressure and high-pressure spools are mounted.

The engine 1 is suspended from the structure of the aircraft that it propels, and that is not shown, by a front suspension 5 and by a rear suspension 6 both being attached to a pylon P or engine mast P itself secured to the structure of the aircraft.

The front suspension 5 is of the type comprising a snout 7 received in an adapted attachment housing of the intermediate casing 3. The rear suspension 6 comprises a beam 8 directly attached to the exhaust casing 4. Such suspensions are well known to those skilled in the art and it is not necessary, in the context of this description, to describe them in greater detail.

On certain components of the device for suspending the turbojet from the aircraft, a system 10 for measuring fatigue has been arranged. More precisely, a system is arranged on each of those components that it is desired to be able to measure the fatigue due to the stresses to which the component is subjected. Each measurement system comprises n sensors Ci (i=1 to n) placed on the component.

In the example of FIG. 1, a measurement system 10 has been provided on the snout 7 of the front suspension 5, on the beam 8 of the rear suspension 6, on each connecting rod connecting the beam 8 of the rear suspension 6 to the intermediate casing $4a$ and to the pylon P.

Figure 2:
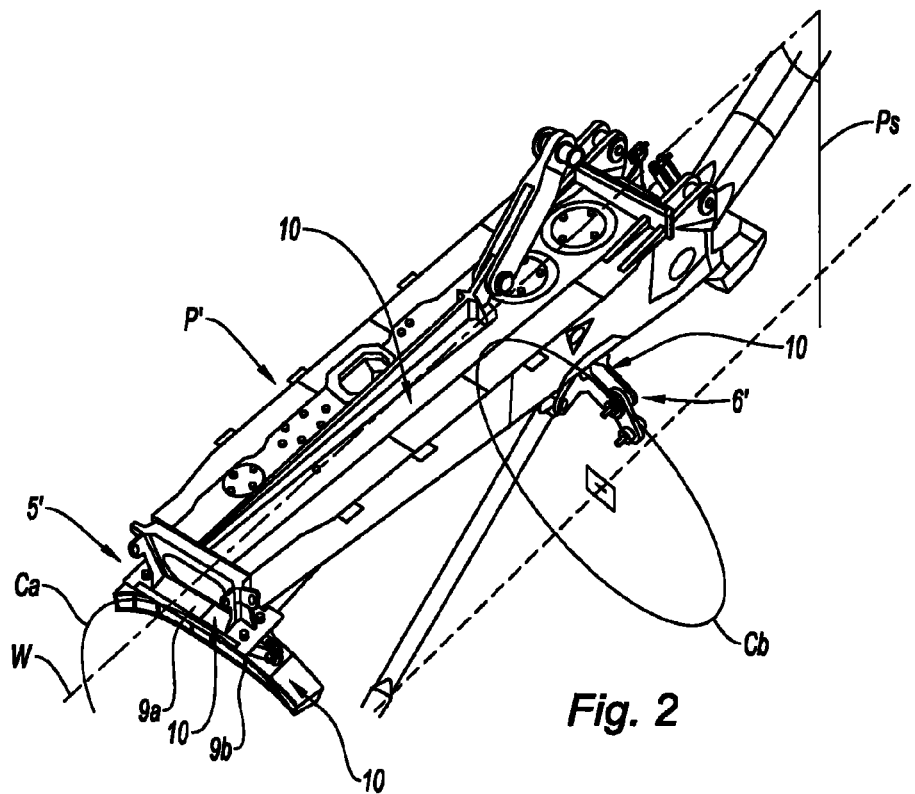
FIG. 2 represents a schematic view in perspective, seen from upstream, of a second type of suspension that can be used on a turbojet.

Shown in FIG. 2 are certain elements involved in the suspension of a turbojet according to a second type of suspension and on which it is possible to provide a system 10 for measuring fatigue according to the invention. FIG. 2 shows only one beam P' and front suspensions 5' and rear suspensions 6' of such a turbojet, these elements being represented alone but in their context, only two circles Ca, Cb having been drawn to represent schematically the casings of the turbojet on which the suspensions 5', 6' are mounted. The front suspension 5' comprises a rectilinear beam $9a$ connected by connecting rods to an intermediate beam $9b$ commonly called a "yoke" by those skilled in the art and itself connected to the intermediate casing of the turbojet by connecting rods; the suspensions of this type are well known in the field. The rear suspension 6' for its part comprises a single beam.

As above, it is desired to be able to estimate the fatigue of certain components of the device for suspending the turbojet from the aircraft. Accordingly a system 10 for measuring fatigue according to the invention is provided on each of the components of which it is desired to monitor the fatigue, for example on the pylon P', on the beam $9a$ of the front suspension 5', on the intermediate beam (yoke) $9b$ of the front suspension 5' and on the rear suspension beam 6'. It is moreover possible to provide measurement systems 10 for certain connecting rods of the suspension device.

In FIG. 1 as in FIG. 2, only the systems 10 have been referenced, the sensors Ci not having been shown because their dimensions are very small.

Finally, it is understood that the system 10 for measuring fatigue of the invention can be put in place on many components of the turbojet or of the aircraft because of its simplicity.

According to one particular embodiment, several distinct measurement systems 10 are installed for one and the same engine, each measurement system 10 being specifically dedicated to the measurement of the fatigue due to the stresses exerted in the direction of a degree of freedom of the engine. An engine comprises six degrees of freedom, typically in translation in three perpendicular directions and in rotation about these directions; these six degrees of freedom can be modeled by six connecting rods working in tension-compression; since the sensors of a measurement system 10 measure the tension-compression forces, each system 10 can monitor the fatigue due to the stresses on a connecting rod. It is therefore possible to provide several systems 10 for the engine, each system 10 measuring the fatigue of one connecting rod; according to one particular embodiment, one system 10 is provided for each connecting rod, all of the degrees of freedom thus being able to be monitored.

The sensors Ci of a measurement system 10 are preferably placed in a zone of the component in which the different locations of the n sensors Ci (i=1 to n) are subjected to one and the same type of deformation and preferably to tension and/or compression stresses. For example, if the system is arranged to measure the fatigue of a connecting rod, the sensors Ci will preferably be placed in the middle of the connecting rod.

Note that if a component is symmetrical relative to a plane and that a system for measuring fatigue is arranged on it in order to measure the fatigue due to the stresses perpendicular to this plane, sensors Ci can be placed on either side of the plane of symmetry, preferably by alternating, from one side to the other, the thresholds of the sensors Ci. Thus, for example, the pylon P' shown in FIG. 2 extending generally along an axis W and being generally symmetrical relative to a plane of symmetry Ps containing this axis W, sensors Ci can be distributed on either side of the plane Ps, alternating the successive thresholds on either side of this plane Ps.

It is possible to envisage using several ways to fasten the sensors Ci to the components of which it is desired to measure the fatigue, for example by bonding, screwing or by embedding them directly in the material. It is also possible to screw to a component a small plate to which the sensors Ci are fastened.

The system 10 for measuring fatigue of the invention will now be described in greater detail, as such and with reference to any component, with reference to FIGS. 3 and 4.

Figure 3:
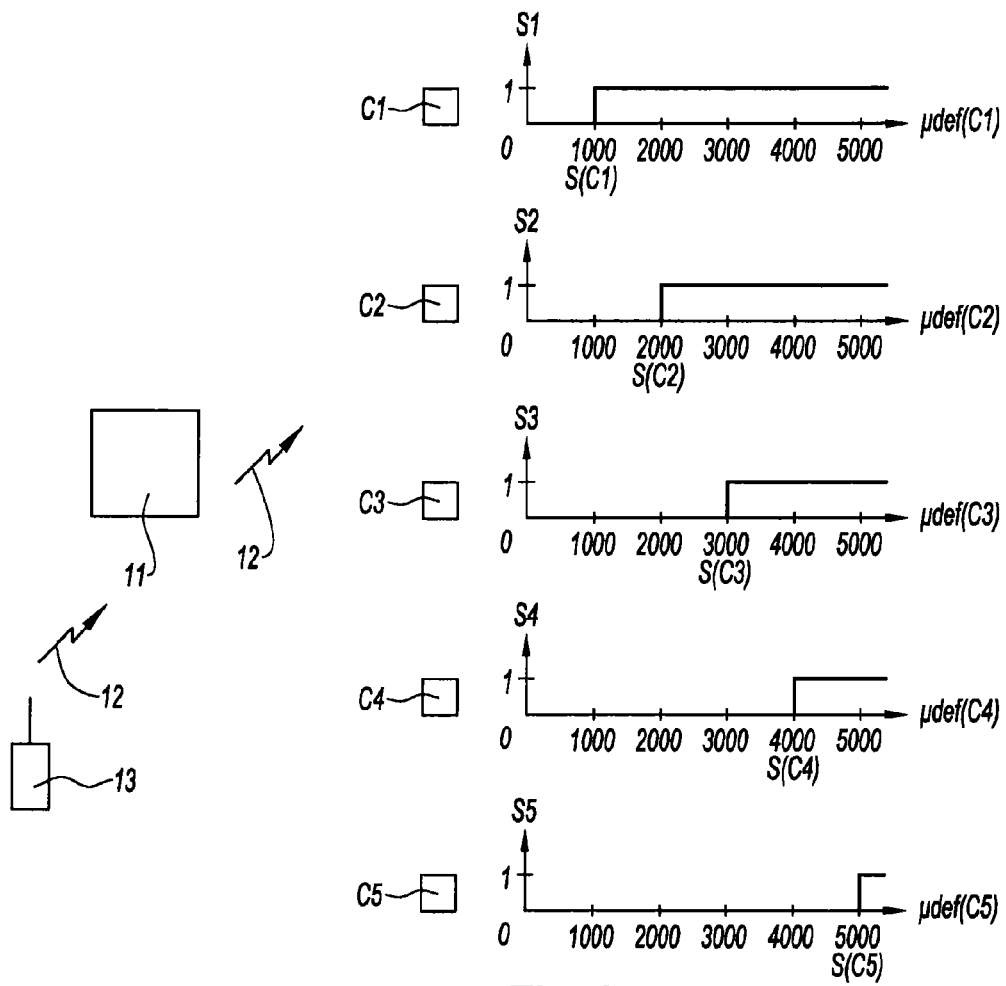
FIG. 3 is a schematic representation of the system of the invention with a representation of the law governing the response of the sensors to the mechanical stresses and FIG. 4 is a histogram representing the data recorded by the sensors of the system of the invention during a determined period of time.
Figure 4:
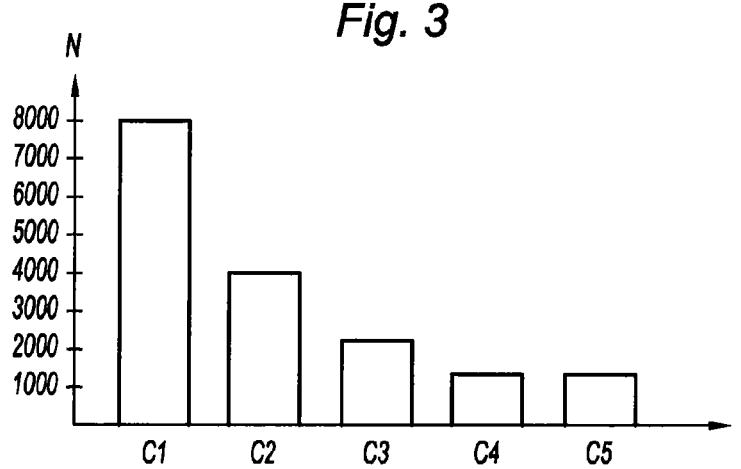

The system 10 comprises a plurality n of stress sensors Ci, in this instance for the examples of FIGS. 3 and 4, five sensors C1, C2, C3, C4, C5 (n=5). The sensors C1-C5 are installed on the component for which it is desired to measure the fatigue resulting from the mechanical stresses that it sustains.

In order to make the description of the system 10 of the invention easier, the values assigned to the sensors are notional and designed only for understanding the operation of the system. Those skilled in the art will adapt the system (in particular the number of sensors, the value of the stress thresholds that they detect and the number of detected thresholds) to the component on which he installs the system 10, in particular as a function of the materials used.

The sensors Ci are in this instance deformation sensors, the deformation of a component in response to a stress being expressed as a magnitude with no unit called "micro-deformation", symbolized by "μdef" and well known to those skilled in the art; this magnitude corresponds to a lengthening related to a unit of length according to the well known formula: $\mu def = \Delta L/L$. For example, a lengthening of 1 mm for a component that is 1 m long corresponds to a deformation of $0.001/1 = 1,000$ μdef.

Thus, the stresses sustained by a material result in deformations of the component and therefore in μdef (in application of Hooke's law). The deformation sensors are therefore stress sensors. It will therefore be easily understood that the rest of the description will use without distinction the concept of stress or of deformation, of stress threshold or of deformation threshold, since the applied stress is deduced directly from the deformation.

Reproduced below as an example is an approximate mapping between the deformation thresholds of the sensors of FIG. 3 (introduced in greater detail below) and the associated stresses for steel (or inconel or "INCO") and titanium; it is clear that the stress associated with a given deformation (and vice versa) is not the same for these two types of materials.

| Steel or INCO | | Titanium | |
| --- | --- | --- | --- |
| Deformation (μdef) | Associated stress (MPa) | Deformation (μdef) | Associated stress (MPa) |
| 1000 | 210 | 1000 | 110 |
| 2000 | 420 | 2000 | 220 |
| 3000 | 630 | 3000 | 330 |
| 4000 | 840 | 4000 | 440 |
| 5000 | 1050 | 5000 | 550 |

Each sensor C1-C5 is arranged to detect a predetermined level or threshold of mechanical stress and to deliver a data signal (in this instance a bit) if this threshold is violated. In other words, the sensors C1-C5 are each sensors of a determined threshold stress and each sensor makes it possible to count the number of occurrences of stresses greater than this threshold stress.

Shown in FIG. 3, opposite each of the sensors C1-C5 of the system 10, is a diagram representative of the signal Si (i=1 to 5) delivered by the sensor Ci as a function of the stress, that is to say the deformation μdef(Ci) (i=1 to 5) that it sustains. As explained above, each sensor Ci (i=1 to 5) delivers a signal Si as a function of the deformation that it sustains:

Si=0 (which corresponds in this instance to an absence of signal) if the deformation μdef(Ci) is below the threshold for triggering the sensor Ci and Si=1 (which corresponds to one bit) if the deformation μdef(Ci) is above the threshold for triggering the sensor Ci.

In this instance, as can be seen in FIG. 3:
the first sensor C1 has a trigger threshold equal to S(C1) =1000 μdef;
the second sensor C2 has a trigger threshold equal to S(C2) =2000 μdef;
the third sensor C3 has a trigger threshold equal to S(C3) =3000 μdef;
the fourth sensor C4 has a trigger threshold equal to S(C4) =4000 μdef;
the fifth sensor C5 has a trigger threshold equal to S(C5) =5000 μdef.

When the component on which the sensors Ci are installed sustains a deformation, each sensor Ci sustains substantially this same deformation. If the deformation that it sustains is below its trigger threshold, the sensor transmits no signal; if the deformation is above its trigger threshold, the sensor transmits a signal (bit). Moreover, in the embodiment described, in the event of prolonged load, a sensor Ci transmits only one bit; a sensor Ci transmits a new bit only if the stress level returns below its threshold S(Ci) before going back over it again.

As an example, let us suppose that the component sustains a deformation equal to 3300 μdef; in this case, the sensors C1, C2 and C3 transmit a bit and the sensors C4 and C5 do not transmit any.

The data of the sensors C1-C5 (that is to say the number of bits that they have each transmitted) during the use of the aircraft that is provided therewith are recorded and stored in a memory of a processing unit 11 of the measurement system 10, this processing unit 11 being able, for example, to be installed close to the zone where the sensors C1-C5 are installed and communicating with them by radio waves 12, as shown schematically in FIG. 3. More precisely, when it transmits a bit, a sensor Ci transfers a data signal by radio waves 12 to the processing unit 11, this signal comprising an identification of the sensor Ci; the processing unit 11 can then increment the counter of the sensor Ci in question. The electronic recording of sensor data is a known practice and it is not necessary here to describe it in detail; it may be used conventionally. The processing unit 11 may be contained in the computer of the turbojet, well known under its acronym of FADEC which means "Full Authority Digital Engine Control". Described here is a data communication between the sensors Ci and the processing unit 11 by radio waves (high frequency or low frequency), but it goes without saying that any other communication means, with, or wireless, irrespective of the protocol, can be envisaged.

Alternatively, the data from the sensors Ci can be recorded directly in means arranged directly in the sensors.

Irrespective of the data-recording means, after a period of usage time, the system comprises data relating to the number of deformations that have been sustained by each sensor C1-C5 and that are higher than their respective thresholds.

FIG. 4 shows a histogram representative of the data recorded by the sensors of the system 10 during a determined period of time (for example from the time the component fitted with the sensors C1-C5 was placed in service). This histogram represents, on the x axis, the sensors C1-C5 in question and, on the y axis, the number N of signals equal to 1 that each sensor has transmitted during the determined period of time.

This shows that the first sensor C1 has transmitted 8000 bits (signifying that it has sustained 8000 deformations higher than its trigger threshold 1000 µdef), the second sensor C2 has transmitted 4000 bits (signifying that it has sustained 4000 deformations higher than its trigger threshold 2000 µdef), the third sensor C3 has transmitted 2000 bits, the fourth sensor C4 has transmitted 1000 bits and the fifth sensor C5 has transmitted 1000 bits.

From the data recorded by the sensors C1-C5 it is possible to compute the total damage $D_{TOTAL}$ that the component has sustained and therefore its fatigue (the fatigue corresponding to the damage).

In a general (and known) manner, the damage D sustained by a component subjected to a determined stress A (or deformation A) is defined by the following formula (the Miner equation):

$$D = n(A)/N(A) \text{ where}$$

n(A) represents the number of occurrences (cycles) of the event leading to the application of the stress (deformation) A and N(A) represents the number of occurrences (cycles) of the event leading to the application of the stress (deformation) A that the component can withstand before it breaks (this value is conventionally determined by virtue of the curves called Wohler curves).

Thus, when the damage D is equal to 1, the component breaks; when the damage is equal to 0, the component is not damaged at all.

The number of signals transmitted by each sensor Ci is representative of the fatigue that it has sustained, since it is a function of the number of occurrences of the various deformations to which the component has been subjected. It is possible to deduce, from the data recorded by the sensors Ci, an equivalent damage Di per sensor Ci; this equivalent damage Di corresponds to the damage resulting from the application of stresses higher than the threshold S(Ci) of the sensor Ci but lower than the higher threshold S(Ci+1).

The laws of fatigue teach that the total damage $D_{TOTAL}$ of a component resulting from all of the stresses that are applied thereto can be broken down in a linear manner into the total of the equivalent damages of each range of stresses. In other words, if all of the stresses are divided into ranges of stresses corresponding to the intervals between the successive thresholds of the sensors Ci, a good approximation of the damage $D_{TOTAL}$ of the component is obtained by the total of the equivalent damages Di for each range of stresses, that is to say $D_{TOTAL} = \Sigma_1^n D_i$.

In order to compute $D_{TOTAL}$, the number n(Ci) of occurrences of stresses included between the threshold S(Ci) of this sensor Ci and the higher threshold S(Ci+1) is computed for each sensor Ci from the data recorded by the sensor Ci (i=1 to 5). The equivalent damage Di of a sensor Ci can then be computed on the basis of this number n(Ci), by applying it to one or more of the stresses representative of the range of stresses in question. Not knowing the exact distribution of the stresses in the range of stresses, it is possible in this instance to make an approximation; several solutions can be envisaged:

it is possible to use an average value of deformation between the two thresholds (µdef(average)=(S(Ci)+S(Ci+1))/2) and to consider that the resulting damage Di is that resulting from n(Ci) occurrences of this average deformation µdef(average);

it is possible to carry out statistical analyses to determine a weighted average to be applied between the thresholds and to use this weighted average;

it is possible, for safety, to take the upper limit (S(Ci+1)) of the range of stresses and to consider that the equivalent damage Di corresponds to n(Ci) occurrences of a deformation corresponding to this higher limit S(Ci+1) (so-called "conservation" assumption).

Other approximations are possible. In the preferred embodiment of the invention, in order to satisfy the most demanding criteria with respect to safety in aviation, the last approximation (conservation assumption) is chosen. The computed deformation Di is therefore greater than the real deformation.

In order to determine the number n(Ci) of occurrences counted by a sensor Ci, it is necessary to subtract from the total sum N(Ci) of the bits of the sensor Ci all the signals that correspond to stresses higher than the higher threshold S(Ci+1) to the threshold S(Ci) of this sensor Ci.

In order to determine all the occurrences n(Ci), we therefore begin with the sensor C5 which has the highest threshold. Therefore, for example in FIG. 4:

n(C5)=N(C5)=1000, so the sensor C5 has counted 1000 stresses higher than its threshold S(C5)=5000 µdef;

n(C4)=N(C4)−N(C5)=0, so the sensor C4 has counted no stresses between its threshold S(C4)=4000 µdef and the higher threshold S(C5) (specifically all the bits of the counter C4 correspond to stresses higher than S(C5) so they are already counted by the sensor C5);

n(C3)=N(C3)−N(C4)=2000−1000=1000, so the sensor C3 has counted 1000 stresses between its threshold S(C3)=3000 µdef and the higher threshold S(C4);

n(C2)=N(C2)−N(C3)=4000−2000=2000, so the sensor C2 has counted 2000 stresses between this threshold S(C2)=2000 µdef and the higher threshold S(C3);

n(C1)=N(C1)−N(C2)=8000−4000=4000, so the sensor C1 has counted 4000 stresses between its threshold S(C1)=1000 µdef and the higher threshold S(C2).

For each of the n(Ci) computed above, an equivalent damage Di for the component (Di=n(Ci)/N(S(Ci+1))) where N(S(Ci+1)) is the number of occurrences of a stress corresponding to the deformation of the higher threshold S(Ci+1) leading to a breakage of the component (see the approximation above).

Finally, the total damage $D_{TOTAL}$ as suffered by the component is, as explained above, equal to the total of the damages corresponding to each range of stress, that is to say $D_{TOTAL} = \Sigma_1^n D_i$ for n sensors.

The system has been explained, as an example, with 5 sensors. It goes without saying that it may include more or fewer sensors and more generally a number n of sensors. The various formulae above are therefore used for i=1 to n.

Once again and in a more synthetic manner, the application of the preferred embodiment of the method of the invention for n sensors will be explained. The method comprises in this case the following steps:

1) the n sensors Ci measure the number of occurrences N(Ci) of stresses higher than their threshold S(Ci);

2) these data N(Ci) are recorded for a time t;

3) for each sensor Ci, based on all of the occurrences N(Ci) (i=1 to n), the number of occurrences n(Ci) corresponding to stresses between the threshold S(Ci) of the sensor Ci and the higher threshold S(Ci+1) is computed according to the formula:

$$n(Cn)=N(Cn);$$

for i<n, n(Ci)=N(Ci)−N(Ci+1);
4) for each sensor Ci, an equivalent damage Di for the component corresponding to the range of stresses between the threshold S(Ci) of the sensor Ci and the higher threshold S(Ci+1) is computed;
5) the total damage $D_{TOTAL}$ of the component is computed according to the formula:

$$D_{TOTAL} = \Sigma_1^n D_i$$

In other words, by virtue of the system and of the method of the invention, it is possible to obtain, for the component fitted with incremental sensors Ci (i=1 to n), each sensor being set on a stress threshold S(Ci) (and the stresses thus having been broken down into n ranges of successive stresses), a complex fatigue spectrum that makes it possible to obtain the total fatigue (total damage $D_{TOTAL}$) based on its breakdown into equivalent fatigues (equivalent damages Di) corresponding to each range of stresses.

It is therefore possible to apply simplified maintenance methods.

For example, an operator may have in his possession a device 13 for receiving the data recorded by the sensors Ci. In the example of the system of FIG. 3, the device 13 is arranged to communicate by radiowaves 12 with the processing unit 11 of the system; any other form of communication may of course be provided.

Naturally, if the system 10 does not comprise a processing unit for the storage of the data measured by the sensors Ci, the device 13 may be arranged to communicate directly with the sensors Ci so that the latter transmit individually to it the data that they have recorded.

The device 13 comprises a processing unit with a computing software program (algorithm) allowing it, based on the recorded data (the bits N(Ci) (i=1 to n) of the sensors Ci), to compute the corresponding damage $D_{TOTAL}$ of the component, according to the method described above.

Therefore, the operator brings his device 13 close to the component (for example a suspension of the airplane), the latter downloads, automatically or on instructions, the data recorded by the sensors Ci and computes the damage $D_{TOTAL}$, that is to say the fatigue, of the suspension, which allows the operator to make a decision in consequence. For example:
- if the damage $D_{TOTAL}$ is between 0 and 0.3, an overhaul is unnecessary;
- if the damage $D_{TOTAL}$ is between 0.3 and 0.8, an overhaul is necessary;
- if the damage $D_{TOTAL}$ is greater than 0.8, the component must be replaced.

It is moreover possible to envisage that the analysis is not made by the operator himself but automatically by the device 13. Thus, if no overhaul is necessary, the device 13 emits no signal (or emits for example a green light) and, if an overhaul is necessary, the device 13 emits an audible signal (or emits for example a red light).

It is also possible to envisage that the information collected by the device 13 is transmitted, automatically or on request of the operator, to a computer server or any other device arranged to receive this information and to process it.

Any other operation can be envisaged depending on the desires of the users. It is possible in particular to envisage that the monitoring of the fatigue of the component is carried out automatically by the processing unit 11 (for example the FADEC) which automatically alerts a third party (such as the pilot of the airplane, its manufacturer, its operator, a computer server or other elements) when a certain level of fatigue is exceeded.

Finally the system 10 of the invention makes it possible to count the stresses to which a component is subjected and consequently to construct a complex fatigue spectrum. The system 10 also makes it possible to have an accurate capture of the history of the events during the use of the component. The sensors with low-amplitude thresholds more particularly give information on the normal use of the component, that is to say on its effective period of use since it was used for the first time. The sensors with high-amplitude thresholds more particularly give information on the exceptional stresses to which the component might have been subjected such as hard landings for example. The system is thus an excellent maintenance tool for the end user of a component.

According to one particular embodiment, it is possible to envisage that the sensors comprise a clock making them deliver a bit at regular intervals, this bit being equal to 0 if the sensor is not subjected to a stress violating its threshold and equal to 1 if the sensor is subjected to a stress violating its threshold. This would be possible with digital sensors.

In the preferred embodiment, it is preferred to use mechanical sensors delivering a signal only in the event of excitation by a stress higher than their threshold; such mechanical sensors have the advantage of being simple to use but also to supply with energy.

Note that the system 10 has been explained in relation to positive deformations (µdef taking only positive values). According to another embodiment, the system may comprise sensors with a positive threshold (µdef>0) and/or sensors with a negative threshold (µdef<0), which makes it possible to count the stresses in one direction (tension) and in the other (compression) for example.

Note that it is possible to provide for several sensors (at least two) to have the same stress threshold. This makes it possible, in the event of failure of one of these sensors, for the other to still be able to count the occurrences of stresses corresponding to this threshold. Incidentally, note that, if some or all of the sensors relating to a threshold are defective, the presence of a plurality of sensors makes it possible to minimize the error, since the stresses of the sensors of the defective threshold will be counted by the sensor of the lower threshold.

Naturally, the higher the number of sensors, the greater the safety in the event of failure of some of them and the more precise is the computation of the total fatigue since the increments between successive thresholds are smaller. The increments may be all identical or be progressive; the value of a progression of increments is that it is possible to have more precise measurements in the most common stress ranges and less precise measurements for the exceptional stresses (which in any case generate very high stresses). Preferably, between 2 and 50 sensors are placed on one component, depending on the precision desired for the determination of the damage it sustains.

For example, the minimum detected deformation may be equal to 1000 µdef (the threshold of the first sensor C1) and the maximum detected deformation equal to 5000 µdef (the threshold of the last sensor Cn) with a space between successive thresholds that is equal to 200 µdef (in this case, 21 sensors are provided of which the thresholds are respectively equal to 1000, 1200, 1400, . . . , 5000).

The system 10 of the invention has been explained as being placed on a component but it could be placed on a structure comprising a plurality of components and allow the fatigue of the assembly to be monitored.

In an aviation application, the sensors should preferably withstand temperatures in a range between −55° C. and 600° C. (in particular for turbojet suspensions) and be able to withstand splattering with oil and fuel. They should also preferably be able to withstand corrosion and dirt and in particular those associated with the spraying of water, of salt, of sand and of sludge. Moreover, advantageously they should withstand nondestructive inspections such as penetrant inspection, the application of eddy currents, of X-rays, etc. Preferably they should have electromagnetic compatibility with various waves (radio, audio, etc.). The sensors should also be able to withstand the mechanical vibrations of the turbojet which may be of the order of several tens of kHz, in particular those due to the rotation of the rotating components of the turbojet (from 0 to 5500 revolutions per minute for the low-pressure spool and from 0 to 20 000 revolutions per minute for the high-pressure spool) and tolerate impacts of from several tens to several tens of thousands of g (9.81 m·s$^{-2}$). Preferably they should also tolerate static and quasi-static deflections under various types of loads.

The sensors should also preferably have a service life at least equal to that of the component on which they are intended to be installed since they are designed to monitor the state of fatigue thereof throughout its service life. For example, their service life could be greater than 60 years or than 70 or 80 000 flight cycles (takeoff-flight-landing).

Preferably, the sensors can sustain more than 10$^9$ occurrences of stresses beyond their threshold. Throughout their use and the application to them of dynamic loads, the sensors must preferably not be adversely affected in their operation.

Preferably, the power supply of the sensors is independent of that of the aircraft.

The system of the invention is particularly advantageous for turbojet suspension devices and in particular the connecting rods of these devices, their beams or else their pylons. The system of the invention may also advantageously be arranged on landing gear of airplanes or on brake bars. In general, it may be arranged on any component that can be instrumentable (that is to say on which it is possible to install sensors) and the use of which causes varied stresses justifying obtaining a complex fatigue spectrum; this is notably the case with the various connecting rods and shackles of a turbojet.

The sensors of the invention make it possible to monitor the various types of fatigue under stresses for example conventionally designated in the Wohler curves for each zone of oligocyclic fatigue (under high stress, where the breakage occurs after a small number of occurrences and is preceded by a notable plastic deformation), for each zone of fatigue (or limited endurance, where the breakage is expected after a number of cycles that increases when the stress decreases), and for each zone of unlimited endurance; naturally, the zone of unlimited endurance is of less value since the component is normally replaced before a breakage can occur because of stresses corresponding to this zone.

According to the preferred embodiment of the invention, the sensors Ci of the system 10 are installed in devices (or sensors) of the MEMS type that have already been explained in the introduction.

It is possible to note that the devices of the MEMS type, because of their miniaturization, comprise micromechanisms of which the response time is extremely short, which provides them with a very rapid reaction time.

Moreover, such devices may be easily housed in the components of the turbojet. They may also be self-powered and therefore be autonomous, which makes them easier to install and provides guaranteed safety of the assembly. The self-powering means of a device of the MEMS type may for example consist of means arranged to convert the ambient energy of the turbojet into electrical energy (for example a microturbine using the surrounding gases to generate electricity and power the device). Moreover, means for processing the data measured by the sensor of the device of the MEMS type can be provided on this same device.

The invention has been described with reference to preferred embodiments, but it goes without saying that other embodiments can be envisaged. In particular, the features of the various embodiments described can be combined together provided that there are no incompatibilities.

The invention claimed is:

1. A system for measuring fatigue of an aircraft component subjected to mechanical stresses, the system comprising:
    a plurality of stress sensors $C_i$ mounted on the aircraft component in which i=1 to n where n is a number of sensors, each sensor being configured to detect a predetermined mechanical stress threshold $S(C_i)$ and to deliver a data signal representative of violation of this threshold;
    means for recording the data signal; and
    means for calculating damage based on the data signal,
    wherein the sensors are configured to detect different thresholds of a same stress, which thresholds are staged so as to compute, based on a number of threshold violation occurrences of each sensor $n(C_n)$, an estimate of fatigue of the aircraft component due to the predetermined mechanical stress,
    wherein each sensor $C_i$ measures a number of occurrences $N(C_i)$ of stress higher than the stress threshold $S(C_i)$, and the number of threshold violation occurrences $n(C_n)$ between the stress threshold of the sensor $S(C_i)$ and a higher stress threshold $S(C_{i+1})$ is computed as $n(C_n)=N(C_n)$; for i<n, $n(C_i)=N(C_i)-N(C_{i+1})$,
    wherein for each sensor $C_i$, an equivalent damage $D_i$ for the aircraft component corresponding to a range of stresses between the stress threshold $S(C_i)$ of the sensor $C_i$ and the higher threshold $S(C_{i+1})$ is computed, and the estimate of fatigue of the aircraft component is calculated based on a sum of the equivalent damage $D_i$ for each sensor $C_i$.

2. The system as claimed in claim 1, further comprising a processing unit comprising the data-recording means, the sensors comprising means for transmitting the data to the processing unit.

3. The system as claimed in claim 1, wherein each sensor comprises data-recording means.

4. The system as claimed in claim 3, further comprising means for transmitting the data to remote means for analyzing the data, configured to compute an estimate of the fatigue of the component.

5. The system as claimed in claim 1, wherein the sensors are sensors of MEMS type.

6. A method for measuring fatigue of an aircraft component subjected to a predetermined mechanical stress, comprising:
    placing a plurality of sensors $C_i$ capable of detecting predetermined thresholds of the predetermined mechanical stress $S(C_i)$ on the aircraft component in which i=1 to n where n is a number of sensors, the sensors being staged relative to one another and each being capable of delivering a data signal representative of violation of its threshold $S(C_i)$ by the stress;

measuring the stress on the aircraft component using the plurality of sensors $C_i$;

recording a number of occurrences N(Ci) of measurements of violation of the threshold $S(C_i)$ for each sensor $C_i$;

computing using a computer, for each sensor, a number of threshold violation occurrences $n(C_n)$ between the stress threshold of the sensor $S(C_i)$ and a higher threshold $S(C_{i+1})$ as $n(C_n)=N(C_n)$; for i<n, $n(C_i)=N(C_i)-N(C_{i+1})$; and computing, based on the number of occurrences, an estimate of fatigue of the aircraft component caused by the predetermined mechanical stress by computing, for each sensor, an equivalent damage $D_i$ for the aircraft component corresponding to a range of stresses between the stress threshold $S(C_i)$ of the sensor $C_i$ and the higher threshold $S(C_{i+1})$ and summing the equivalent damage $D_i$ for each sensor $C_i$.

7. The method as claimed in claim 6, wherein:

for each threshold, based on the total number of occurrences, the number of occurrences of measurements of violation of the threshold and that are below the higher threshold are computed; and for each interval between two consecutive thresholds, an equivalent fatigue of the component corresponding to application of a number of stresses corresponding to the number of computed occurrences and of a stress value equal to that of the higher threshold is computed, the equivalent fatigues computed for each interval of thresholds are added together to obtain total fatigue of the component.

8. The method as claimed in claim 6, wherein the sensors are configured to detect different thresholds of a same stress, which thresholds are staged so as to compute, based on the number of threshold violation occurrences of each sensor $n(C_n)$, an estimate of fatigue of the component due to the predetermined mechanical stress.

9. The system as claimed in claim 1, wherein:

a request to transmit the data recorded by the system is transmitted to the system;

the data is received; and based on the data, an estimate of the fatigue of the component due to each of the mechanical stresses is computed.

10. The system as claimed in claim 9, wherein the request is transmitted and the data are received wirelessly by a portable transmission/receiving device.

11. The system as claimed in claim 1, further comprising a device which provides an alert based on the fatigue of the aircraft component.

12. The method as claimed in claim 6, further comprising providing an alert based on the fatigue of the aircraft component.

\* \* \* \* \*